US011660178B2

(12) United States Patent
Sniffin et al.

(10) Patent No.: US 11,660,178 B2
(45) Date of Patent: May 30, 2023

(54) VENTRAL HERNIA DEFECT CLOSURE

(71) Applicant: Covidien LP, Mansfield, MA (US)

(72) Inventors: Kevin Sniffin, Roxbury, CT (US); Gregory Fischvogt, Denver, CO (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 226 days.

(21) Appl. No.: 16/423,368

(22) Filed: May 28, 2019

(65) Prior Publication Data
US 2019/0274807 A1  Sep. 12, 2019

Related U.S. Application Data

(62) Division of application No. 15/157,442, filed on May 18, 2016, now Pat. No. 10,342,651.

(Continued)

(51) Int. Cl.
*A61F 2/00* (2006.01)
*A61B 17/068* (2006.01)
(Continued)

(52) U.S. Cl.
CPC .......... *A61F 2/0063* (2013.01); *A61B 17/064* (2013.01); *A61B 17/068* (2013.01); *A61B 17/083* (2013.01); *A61B 17/0466* (2013.01); *A61B 2017/00004* (2013.01); *A61B 2017/044* (2013.01); *A61B 2017/0648* (2013.01); *A61B 2017/0649* (2013.01); *A61F 2002/0068* (2013.01); *A61F 2002/0072* (2013.01); *A61F 2230/0069* (2013.01)

(58) Field of Classification Search
CPC . A61B 17/0466; A61B 17/064; A61B 17/068; A61B 17/083; A61B 2017/00004; A61B 2017/044; A61B 2017/0648; A61B 2017/0649; A61F 2002/0068; A61F 2002/0072; A61F 2230/0069; A61F 2/0063
See application file for complete search history.

(56) References Cited

U.S. PATENT DOCUMENTS 5,582,616 A  12/1996 Bolduc et al.
5,810,855 A  9/1998 Rayburn et al.
(Continued)

FOREIGN PATENT DOCUMENTS

EP   2853231 A1   4/2015
WO   2006048885 A1   5/2006

OTHER PUBLICATIONS

European Search Report EP16172912 dated Feb. 20, 2017.
(Continued)

*Primary Examiner* — Brooke Labranche
(74) *Attorney, Agent, or Firm* — Carter, DeLuca & Farrell LLP

(57) ABSTRACT

A tissue defect closure system includes an endoscopic surgical fixation device and an implant. The endoscopic surgical fixation device includes a handle assembly and an elongated outer tube having a distal end and including a plurality of fasteners disposed therein. The implant includes an elongated hollow body having a proximal end and a distal end, and defines an elongated pocket therein. The elongated pocket is dimensioned to engage the elongated outer tube of the endoscopic surgical fixation device.

20 Claims, 9 Drawing Sheets

Related U.S. Application Data

(60) Provisional application No. 62/170,897, filed on Jun. 4, 2015.

(51) Int. Cl.
  *A61B 17/064* (2006.01)
  *A61B 17/08* (2006.01)
  *A61B 17/00* (2006.01)
  *A61B 17/04* (2006.01)

(56) References Cited

U.S. PATENT DOCUMENTS

| | | |
|---|---|---|
| 5,922,026 A | 7/1999 | Chin |
| 7,758,612 B2 | 7/2010 | Shipp |
| 7,867,252 B2 | 1/2011 | Criscuolo et al. |
| 8,114,099 B2 | 2/2012 | Shipp |
| 8,216,272 B2 | 7/2012 | Shipp |
| 8,282,670 B2 | 10/2012 | Shipp |
| 8,382,778 B2 | 2/2013 | Criscuolo et al. |
| 2008/0125869 A1* | 5/2008 | Paz .................. A61F 2/0045 623/23.72 |
| 2012/0035629 A1 | 2/2012 | Sherwinter |
| 2013/0317527 A1 | 11/2013 | Jacinto et al. |
| 2015/0351768 A1* | 12/2015 | Kahana .................. A61B 17/11 606/153 |
| 2016/0310146 A1* | 10/2016 | Levy .................. A61B 17/0485 |

OTHER PUBLICATIONS

European Office Action dated Jan. 25, 2018 issued in corresponding EP Application No. 16172912.4.
Chinese Office Action dated Mar. 23, 2020 issued in corresponding CN Appln No. 2016103943266.
European Examination Report dated Jul. 13, 2020 issued in corresponding EP Appln. No. 16172912.4.

\* cited by examiner

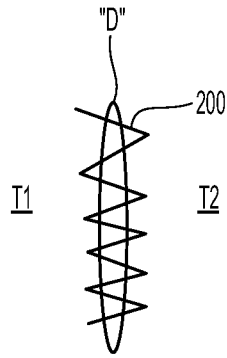
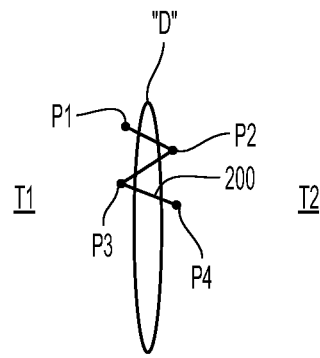
*Fig. 9A*  *Fig. 9B*
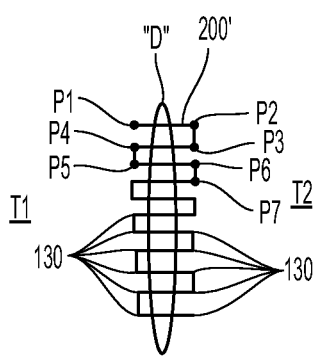
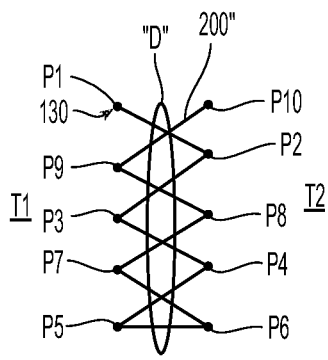
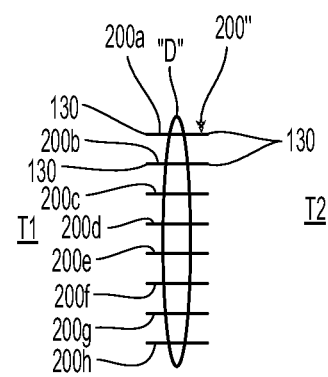
*Fig. 10A*  *Fig. 10B*  *Fig. 10C*
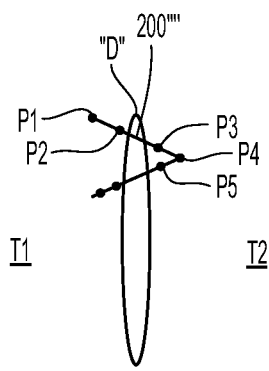
*Fig. 10D*

VENTRAL HERNIA DEFECT CLOSURE

CROSS-REFERENCE TO RELATED APPLICATIONS

This application is a Divisional of U.S. patent application Ser. No. 15/157,442 filed May 18, 2016, which claims the benefit of and priority to U.S. Provisional Patent Application No. 62/170,897, filed Jun. 4, 2015, and the disclosures of each of the above-identified applications are hereby incorporated by reference in their entirety.

BACKGROUND

Techniques for repairing damaged or diseased tissue are widespread in medicine. Wound closure devices, such as sutures and staples, as well as other repair devices like mesh and patch reinforcements, are frequently used for repair. For example, in the case of hernias, a surgical mesh or patch is commonly used to reinforce an abdominal wall. Typically, sutures, staples, and/or tacks are utilized to fix the surgical mesh or patch to surrounding tissue. Accordingly, various surgical procedures require instruments capable of applying fasteners to tissue to form tissue connections or to secure objects to tissue.

Minimally invasive, e.g., endoscopic or laparoscopic, surgical procedures are currently available to repair a hernia. In laparoscopic procedures, surgery is performed in the abdomen through a small incision while in endoscopic procedures, surgery is performed through endoscopic tubes or cannulas inserted through small incisions in the body. Laparoscopic and endoscopic procedures generally utilize long and narrow instruments capable of reaching remote regions within the body and configured to seal with the incision or tube they are inserted through. Additionally, the instruments must be capable of being actuated remotely, that is, from outside the body.

Currently, minimally invasive surgical techniques for hernia repair utilize surgical fasteners, e.g., surgical tacks, staples, and clips, to secure a mesh to tissue to provide reinforcement and structure for encouraging tissue ingrowth. Surgical fasteners are often applied through an elongate instrument for delivery to the mesh, and are manipulated from outside a body cavity.

SUMMARY

The present disclosure is directed to a tissue defect closure system including an endoscopic surgical fixation device and an implant slidingly engaged with the endoscopic surgical fixation device that increases the speed, ease, and quality of minimally invasive tissue defect closure (e.g., ventral hernia repair).

In one aspect of the present disclosure, a tissue defect closure system includes an endoscopic surgical fixation device and an implant. The endoscopic surgical fixation device includes a handle assembly and an elongated outer tube having a distal end and including a plurality of fasteners disposed therein. The implant includes an elongated hollow body having a proximal end and a distal end, and defines an elongated pocket therein. The elongated pocket is dimensioned to engage the elongated outer tube of the endoscopic surgical fixation device. The proximal end of the elongated hollow body may be open and the distal end of the elongated hollow body may be closed.

In some embodiments, the elongated pocket of the implant includes an inner dimension that is complementary in size and shape with an outer surface of the elongated outer tube of the endoscopic surgical fixation device such that the implant is maintained in slidable contact with the elongated outer tube. In certain embodiments, the elongated pocket includes an inner dimension that is adjustable to conform to an outer dimension of the elongated outer tube of the endoscopic surgical fixation device.

The implant may be formed from a collapsible mesh fabric. In some embodiments, the collapsible mesh fabric is a knitted, braided, woven, or non-woven fibrous structure. In certain embodiments, the collapsible mesh fabric is a biaxial or triaxial braided structure.

The tissue defect closure system may include a leash extending proximally from the proximal end of the elongated hollow body of the implant. In some embodiments, the leash includes an elongated flat body, and in some embodiments, the leash includes an elongated rounded body. In certain embodiments, the leash includes a proximal end terminating in a loop.

The plurality of fasteners disposed within the elongated outer tube of the endoscopic surgical fixation device may be selected from the group consisting of clips, tacks, coils, anchors, and staples.

In another aspect of the present disclosure, a method of closing a tissue defect includes: placing a distal end of an implant against a first tissue located on a first side of a tissue defect, the implant including an elongated hollow body defining an elongated pocket therein that is disposed over an elongated outer tube of an endoscopic surgical fixation device such that the distal end of the elongated hollow body of the implant is disposed adjacent the distal end of the elongated outer tube; firing at least one first fastener from the endoscopic surgical fixation device, at least partially through the distal end of the implant, and into the first tissue such that the at least one first fastener secures the implant to the first tissue at one or more first fixation points; moving the distal end of the elongated outer tube of the endoscopic surgical fixation device towards a second tissue located on a second side of the tissue defect such that a portion of the implant proximal of the distal end of the implant is positioned against the second tissue and the implant bridges the tissue defect at a first bridge; and firing at least one second fastener from the endoscopic surgical fixation device, at least partially through the implant, and into the second tissue such that the at least one second fastener secures the implant to the second tissue at one or more second fixation points.

In some embodiments, moving the distal end of the elongated outer tube of the endoscopic surgical fixation device towards the second tissue includes sliding the distal end of the elongated outer tube proximally within the elongated pocket of the implant relative to the distal end of the implant.

In some embodiments, placing the distal end of the implant against the first tissue may include pulling a proximal end of the implant proximally to put tension on the implant. In some embodiments, moving the distal end of the elongated outer tube of the endoscopic surgical fixation device towards the second tissue further includes pulling a proximal end of the implant proximally to put tension on the implant and to approximate edges of the tissue defect prior to firing the at least one second fastener. In certain embodiments, pulling the proximal end of the implant further includes pulling on a leash that is secured to and extends from the proximal end of the implant.

The method may further include: moving the distal end of the elongated outer tube of the endoscopic surgical fixation device back to the first side of the tissue defect such that a portion of the implant proximal of the one or more second fixation points is positioned against the first tissue in spaced relation relative to the one or more first fixation points and the implant bridges the tissue defect at a second bridge; and firing at least one third fastener from the endoscopic surgical fixation device, at least partially through the implant, and into the first tissue such that the at least one third fastener secures the implant to the first tissue at one or more third fixation points.

The method may also further include: moving the distal end of the elongated outer tube of the endoscopic surgical fixation device back to the second side of the tissue defect such that a portion of the implant proximal of the one or more third fixation points is positioned against the second tissue in spaced relation relative to the one or more second fixation points and the implant bridges the tissue defect at a third bridge; and firing at least one fourth fastener from the endoscopic surgical fixation device into the second tissue such that the at least one fourth fastener secures the implant to the second tissue at one or more fourth fixation points.

In some embodiments, moving the distal end of the elongated outer tube of the endoscopic surgical fixation device back to the first side of the tissue defect and/or moving the distal end of the elongated outer tube of the endoscopic surgical fixation device back to the second side of the tissue defect includes sliding the distal end of the elongated outer tube proximally within the elongated pocket of the implant.

The method may further include pulling on a leash extending from a proximal end of the implant to put tension on the implant and to approximate edges of the tissue defect prior to at least one firing the at least one second fastener, firing the at least one third fastener, and firing the at least one fourth fastener.

The method may further include folding the implant about one of the one or more second fixation points such that the implant at least partially overlaps itself prior to moving the distal end of the elongated outer tube of the endoscopic surgical fixation device back to the first side of the tissue defect.

In some embodiments, firing the at least one first fastener includes firing at least two first fasteners in spaced relation relative to each other, and in some embodiments, firing the at least one second fastener includes firing at least two second fasteners in spaced relation relative to each other.

In yet another aspect of the present disclosure, an implant includes an elongated hollow body adapted to close a tissue defect. The elongated hollow body has an open proximal end and a closed distal end, and defines an elongated pocket therein having an adjustable inner dimension. The elongated hollow body may be formed from a collapsible mesh and/or may include a leash secured to the proximal end of the elongated hollow body.

Other aspects, features, and advantages will be apparent from the description, drawings, and the claims.

BRIEF DESCRIPTION OF THE DRAWINGS

Various aspects of the present disclosure are described hereinbelow with reference to the drawings, which are incorporated in and constitute a part of this specification, wherein:

FIGS. 9A and 9B are schematic illustrations of the tissue defect closure pattern of FIGS. 4-8;

FIGS. 10A-10D are schematic illustrations of tissue defect closure patterns.

Corresponding reference characters indicate corresponding parts throughout the drawings.

DETAILED DESCRIPTION

In this disclosure, the term "proximal" refers to the portion of a structure closer to a clinician, while the term "distal" refers to the portion of the same structure further from the clinician. As used herein, the term "subject" refers to a human patient or other animal. The term "clinician" refers to a doctor, nurse, or other care provider and may include support personnel.

Figure 1:
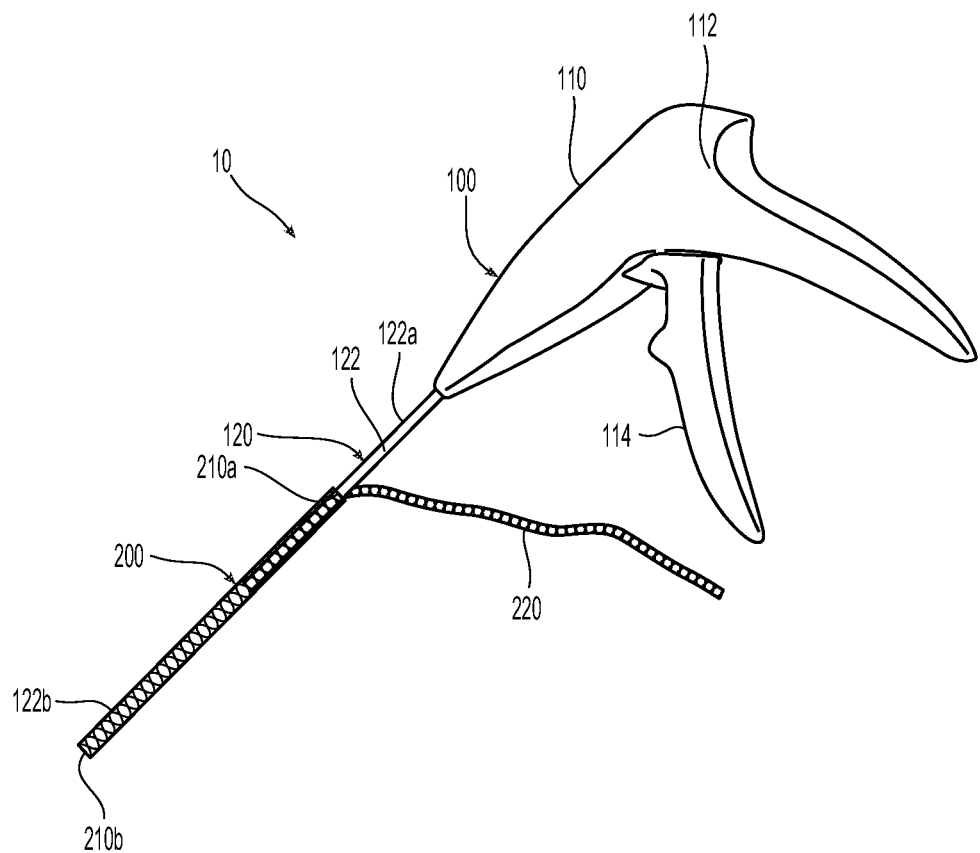
FIG. 1 is a perspective side view of a tissue defect closure system including an endoscopic surgical fixation device and an implant.
Figure 2:
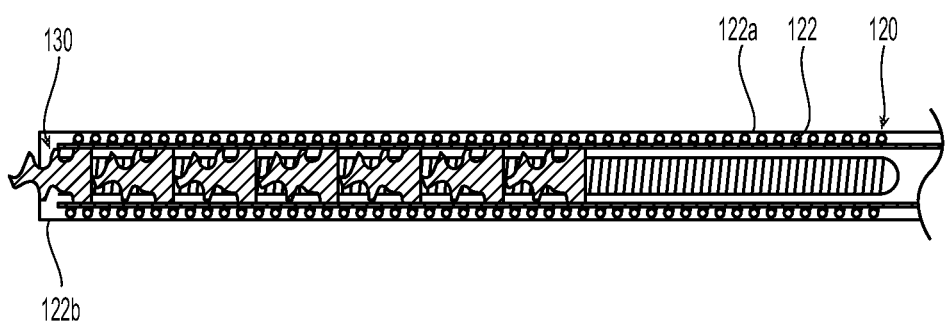
FIG. 2 is a cross-sectional view of a distal end portion of an elongated outer tube of the endoscopic surgical fixation device of FIG. 1.

Referring now to FIGS. 1 and 2, a tissue defect closure system 10 in accordance with the present disclosure includes an endoscopic surgical fixation device 100 and an implant 200 slidingly engaged with the endoscopic surgical fixation device 100. The endoscopic surgical fixation device 100 may be any endoscopic surgical device configured to store and selectively release or fire surgical fasteners 130 therefrom. The surgical fasteners 130 may be any biocompatible fixation device configured to affix a portion of the implant 200 to tissue, such as, for example, clips, tacks, coils, anchors, and staples.

The endoscopic surgical fixation device 100 includes a handle assembly 110 and an endoscopic fastener retaining/advancing assembly 120 extending from the handle assembly 110. The endoscopic fastener retaining/advancing assembly 120 includes an elongated outer tube 122 having an outer surface 122a and an interior that is configured to store and selectively release or fire a plurality of fasteners 130 therefrom through a distal end 122b of the elongated outer tube 122. Handle assembly 110 includes a handle housing 112 which supports a drive train (not shown) therein and a trigger 114 pivotably connected to the handle housing 112 such that, in operation, as the trigger 114 is actuated (e.g., squeezed), the drive train is actuated to effect advancement and/or firing of the fastener(s) 130.

In some embodiments, the endoscopic surgical fixation device is a surgical tack applier including a plurality of anchors disposed within the elongated outer tube. In some embodiments, the endoscopic surgical fixation device is a surgical stapler that is configured and adapted to releasably and selectively receive a disposable loading unit or a single use loading unit which includes a plurality of staples. For a detailed discussion of examples of endoscopic surgical fixation devices and/or fasteners which may be utilized in the system of the present disclosure, reference may be made to U.S. Pat. Nos. 5,582,616, 7,758,612, 7,867,252, 8,114, 099, 8,216,272, 8,282,670, and 8,382,778, the entire contents of each of which are incorporated by reference herein. Other examples of endoscopic surgical fixation devices include devices, such as, ReliaTack™ Fixation Device, AbsorbaTack™ Fixation Device, ProTack™ Fixation Device, Endo Universal™ Stapler, Multifire Endo Hernia™ Stapler, Stat Tack™ Fixation Device, Tacker Fixation Device, and MultiFire VersaTack™ Stapler, all available through Covidien.

Figure 3:
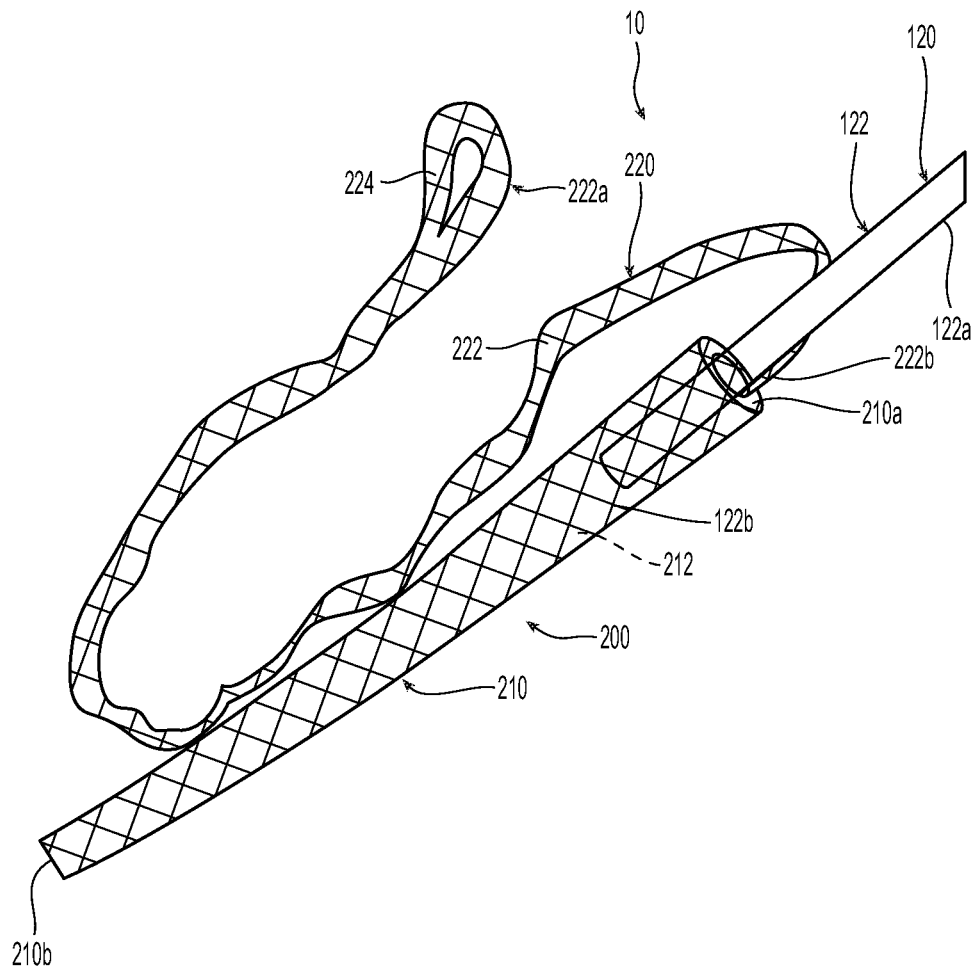
FIG. 3 is a perspective view of a distal end portion of the endoscopic surgical fixation device and the implant of FIG. 1.

Turning now to FIG. 3, an implant, in the form of a collapsible mesh fabric, is shown generally as 200. The implant 200 includes an elongated hollow body 210 having an open proximal end 210a and a closed distal end 210b. An inner surface (not explicitly shown) of the elongated hollow body 210 defines an elongated pocket 212 that is dimensioned to receive the elongated outer tube 122 of the endoscopic surgical fixation device 100. The pocket 212 has an inner dimension configured to be complementary in size and shape with the outer surface 122a of the elongated outer tube 122 such that when the outer surface 122a of the elongated outer tube 122 is received within the elongated pocket 212 of the implant, the implant 200 is maintained in slidable contact with the elongated outer tube 122.

The collapsible mesh fabric of the implant 200 may be a knitted, braided, woven, or non-woven fibrous structure. Additionally or alternatively, the material may be homogeneous along the entire length of the implant 200 or may differ along a length of the elongated hollow body 210. Further, the implant 200 may be a composite including a fibrous structure which may be combined with a porous or non-porous film, foam, or gel sheet over the entirety or a portion of the fibrous structure. These various forms may be used alone or in combination with one another.

The collapsible mesh fabric provides the implant 200 with a flexible structure such that the implant 200 may assume a variety of shapes. For example, the collapsible mesh fabric of the implant 200 allows the elongated pocket 212 of the implant 200 to conform to the shape of the elongated outer tube 122 of the endoscopic surgical fixation device 100. Accordingly, the elongated hollow body 210 of the implant 200 may have a generally flat profile and may be expanded to have, for example, a tubular, ovular, elliptical, or rectangular shape, among other shapes that correspond with the shape of the elongated outer tube 122 of the endoscopic surgical fixation device 100. As another example, the collapsible mesh fabric of the implant 200 allows the implant 200 to be bent and/or folded onto itself so that a clinician may manipulate the implant 200 into a desired shape or pattern, as described in further detail below.

In some embodiments, the elongated hollow body 210 of the implant 200 may be formed from a biaxial or triaxial braid such that the elongated hollow body 210 may be axially compressed to enlarge the inner dimension of the elongated pocket 212 and axially stretched to narrow the inner dimension of the elongated pocket 212 to conform the implant 200 to the shape and size of the outer surface 122a of the elongated outer tube 122 of the endoscopic surgical fixation device 100. Such a configuration can accommodate a variety of surgical instruments having different shapes and sizes, and allows the clinician to customize the inner dimension of the elongated pocket 212 of the implant 200 to conform to an outer dimension of a variety of surgical instruments.

The implant 200 can be in any form that has sufficient strength to reinforce a defect in tissue. The implant 200 can be made of any biocompatible bioabsorbable or non-bioabsorbable material. Where temporary support of a tissue defect is needed, a bioabsorbable material may be used to form all or part of the implant 200. Where permanent support of the tissue defect is needed, the implant 200 may be made entirely, or in part, of a non-bioabsorbable material. A combination of bioabsorbable and non-bioabsorbable materials may be used to form the implant 200.

An extension or leash 220 extends from the proximal end 210a of the elongated hollow body 210 of the implant 200. The leash 220 includes an elongated body 222 having a proximal end 222a for gripping and handling by a clinician and a distal end 222b affixed to the proximal end 210a of the elongated hollow body 210. In embodiments, the proximal end 222a of the elongated body 222 includes a loop 224 for ease in gripping and handling by the clinician. The leash 220 may be any elongated structure such as, for example, a string, a cord, a cable, a suture, a band, or a belt, among other elongated structures within the purview of one skilled in the art. The elongated body 222 of the leash 220 may be flat or rounded (e.g., tubular, ovular, elliptical, rectangular, etc.), and more than one leash may be attached to the implant 200. The leash 220 may be formed from the same material as the implant 200 or may be formed from a different material. In some embodiments, the leash 220 is integrally formed with the elongated hollow body 210.

To assemble the tissue defect closure system of the present disclosure, the open proximal end 210a of the elongated hollow body 210 of the implant 200 is initially placed over the distal end 122b of the elongated outer tube 122 of the endoscopic surgical fixation device 100 such that the elongated pocket 212 of the implant 200 receives the elongated outer tube 122 of the endoscopic surgical fixation device 100, as shown in FIG. 3. The implant 200 is then slid proximally until the closed distal end 210b engages the distal end 122b of the elongated outer tube 122 of the endoscopic surgical fixation device, as shown in FIG. 1. The leash 220 extends proximally to allow a clinician to pull and/or maintain tension on the implant 200.

Figure 4:
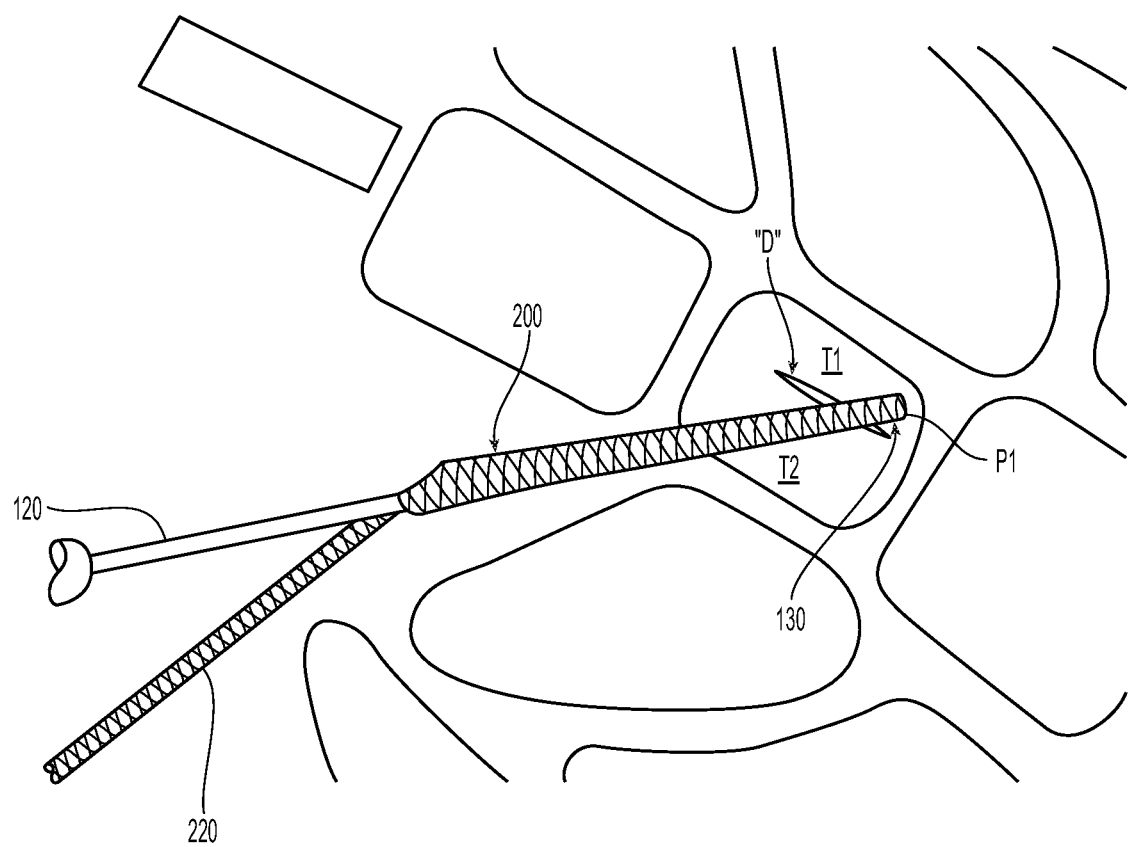
FIGS. 4-8 are perspective views of the tissue defect closure system of FIG. 1 shown closing a tissue defect.

As shown in FIG. 4, in conjunction with FIG. 1, in an exemplary method of use of the assembled tissue defect closure system 10, the distal end 122b of the elongated outer tube 122 of the endoscopic surgical fixation device 100 is positioned adjacent tissue "T1" on a first side of a tissue defect "D" (referred to herein as first tissue "T1") such that the implant 200 is placed against the first tissue "T1." A fastener 130 is fired through the distal end 122b of the elongated outer tube 122, through the implant 200, and into the first tissue "T1" securing the implant 200 to the first tissue "T1" at a first fixation point "P1." Prior to and/or during firing, a clinician can maintain placement of and/or tension on the implant 200 by pulling on the leash 220.

Figure 5:
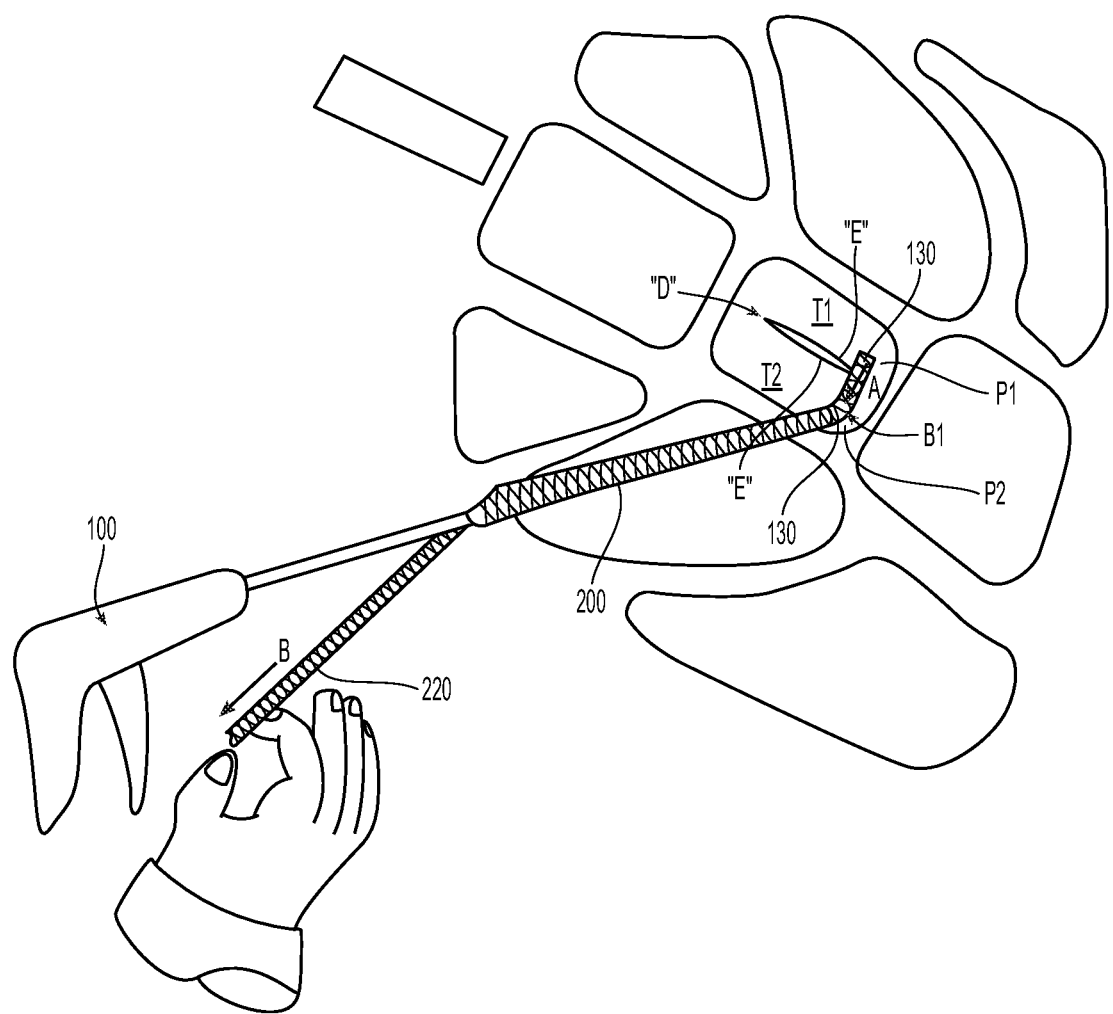

As shown in FIG. 5, the endoscopic surgical fixation device 100 is then moved towards tissue "T2" on a second side of the tissue defect "D" (referred to herein as second tissue "T2") in the direction of arrow "A." During this movement of the endoscopic surgical fixation device 100 towards the second tissue "T2," the distal end 122b of the elongated outer tube 122 is slid proximally with respect to the distal end 210b of the implant 200 thereby freeing the distal portion of the implant 200 from the endoscopic surgical fixation device 100 and allowing the distal portion of the implant 200 to bridge the tissue defect "D." The distal end 122b of the elongated outer tube 122, now having a portion of the implant proximal of the distal end 210b of the implant 200 positioned adjacent the distal end 122b of the elongated outer tube 122, may then be placed against the second tissue "T2" on the second side of the tissue defect "D" such that another fastener 130 may be fired from the endoscopic surgical fixation device 100, out through the distal end 122b of the elongated outer tube 122, through the implant 200, and into the second tissue "T2" thereby securing the implant 200 to the second tissue "T2" at a second fixation point "P2." The leash 220 may be pulled by the clinician in the direction of arrow "B" to bring the edges "E" of the tissue defect "D" together during movement towards the second tissue "T2" and/or prior to firing of the endoscopic surgical fixation device 100. Accordingly, implant 200 bridges the tissue defect "D" at a first bridge "B1" which extends between the first and second fixation points "P1" and "P2."

Figure 6:
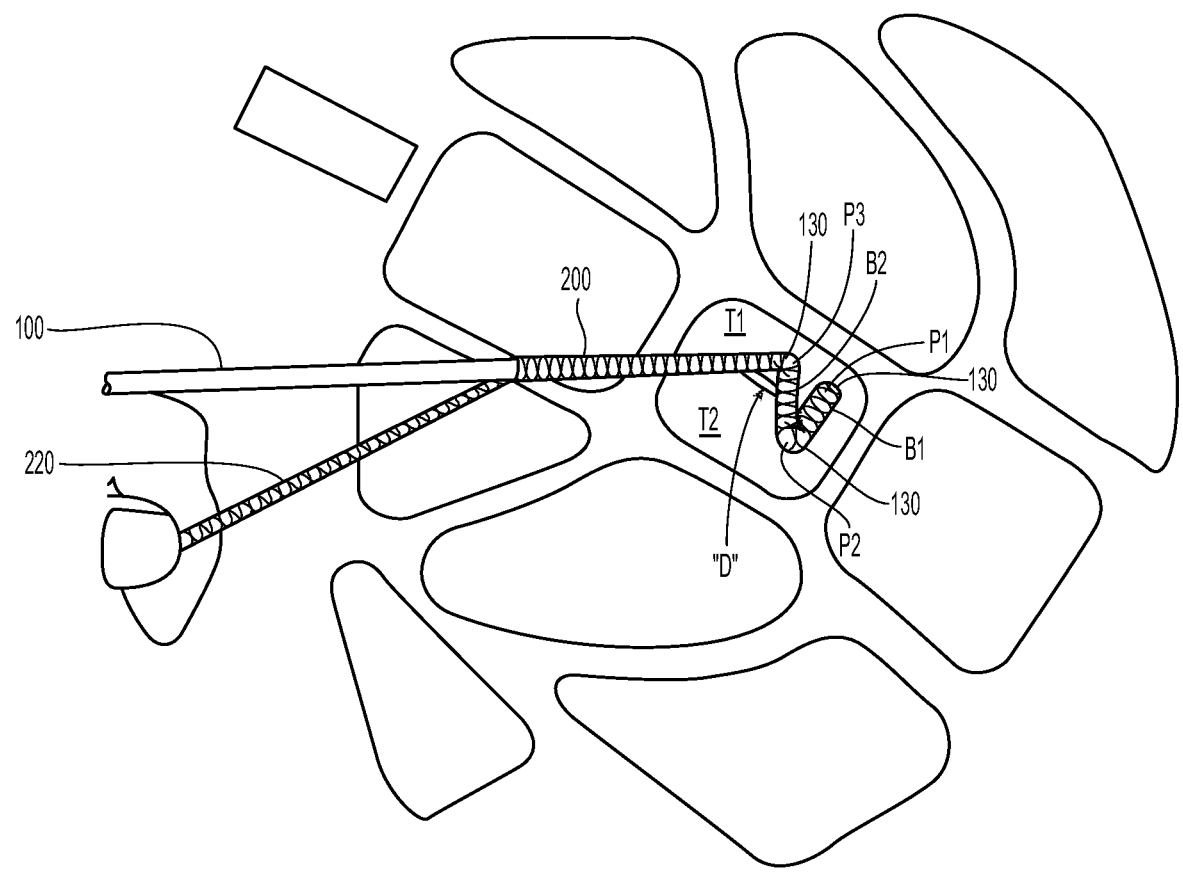

As shown in FIG. 6, the endoscopic surgical fixation device 100 may then be moved back towards the first tissue "T1" on the first side of the tissue defect "D" by, for example, folding the implant 200 such that the implant 200 at least partially overlaps itself about the second fixation point "P2." During movement of the endoscopic surgical fixation device 100 back towards the first tissue "T1," the distal end 122b of the elongated outer tube 122 is slid proximally within the elongated pocket 212 of the implant 200 away from the second fixation point "P2." The distal end 122b of the elongated outer tube 122 may then be placed against the first tissue "T1" on the first side of the tissue defect "D" in spaced relation relative to the fastener 130 at the first fixation point "P1," and a fastener 130 may be fired from the endoscopic surgical fixation device 100 into the first tissue "T1" thereby securing the implant 200 to the first tissue "T1" at a third fixation point "P3." Accordingly, the implant 200 bridges the tissue defect "D" at a second bridge "B2" which extends between the second and third fixation points "P2" and "P3." It should be understood that the leash 220 may be pulled to vary the tension on the implant 200 and/or tissue defect "D" as needed before, during, and/or after firing of the endoscopic surgical fixation device 100.

Figure 7:
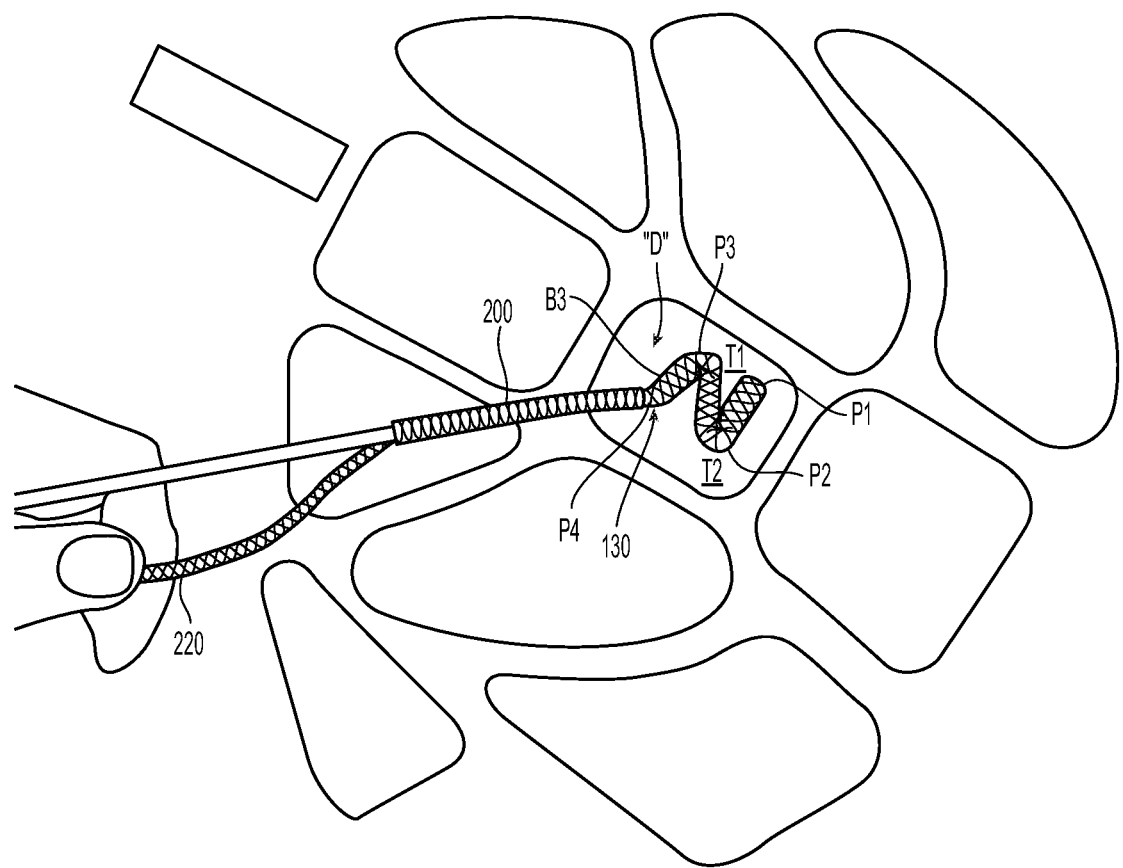
Figure 8:
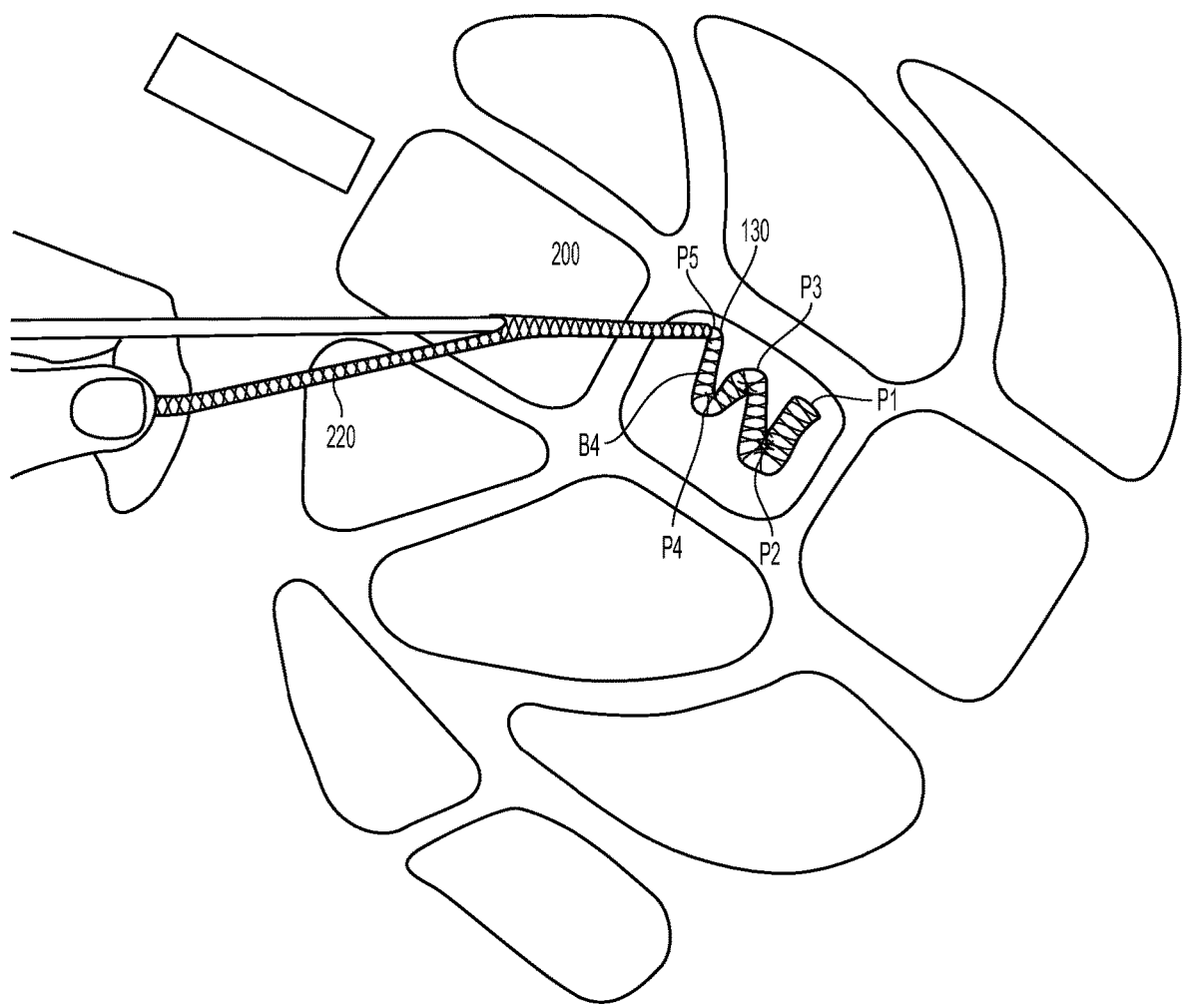

As shown in FIGS. 7 and 8, the process of moving the endoscopic surgical fixation device 100 and firing fasteners 130 through the implant 200 and into the first and second tissues "T1" and "T2" to secure portions of the implant 200 across the tissue defect "D" at subsequent fixation points (e.g., a fourth fixation point "P4" which forms a third bridge "B3" with the third fixation point "P3" (FIG. 7) and a fifth fixation point "P5" which forms a fourth bridge "B4" with the fourth fixation point "P4" (FIG. 8)) may be repeated until the tissue defect "D" is closed. Additionally, it should be understood that the leash 220 may be pulled to bring the edges "E" (FIG. 5) of the tissue defect "D" together as well as maintaining tension on the implant 200 during the closure method, as described above. As schematically shown in FIGS. 9A and 9B, the implant 200 may be secured to tissue in a zig-zag pattern at individual consecutive fixation points (e.g., "P1-P4") on alternating tissue sides "T1" and "T2" of a tissue defect "D."

While certain embodiments have been described, other embodiments are possible.

For example, while the fixation points of the implant are shown in a zig-zag pattern, it should be understood that a variety of patterns may be made to close a tissue defect. Moreover, it should be understood that while the implant has been described as being fastened to tissue at a plurality of single fixation points consecutively disposed on alternating opposed sides of a tissue defect, other fixation patterns are additionally or alternatively possible. Exemplary patterns are shown in FIG. 10A-10D.

Referring now to FIG. 10A, an implant 200' may be placed across a tissue defect "D" in an S-shaped configuration. In such a configuration, implant 200' may be fastened to the first and second tissues "T1" and "T2," which are disposed on opposed sides of the tissue defect "D," at a plurality of fixation points (e.g., "P1-P7") via fasteners 130. The implant 200' is initially secured at a first fixation point "P1" to the first tissue "T1" and then secured to the second tissue "T2" at two second fixation points "P2" and "P3" that are in spaced relation relative to each other. The implant 200' is then secured to the first tissue "T1" at two third fixation points "P4" and "P5" before crossing back over to the second tissue "T2" where the implant 200' is secured at two fourth fixation points "P6" and "P7." This process may be repeated until the tissue defect "D" is closed.

FIG. 10B illustrates an implant 200'' in a cross-over zig-zag configuration. In such a configuration, the implant 200'' may be fastened to the first and second tissues "T1" and "T2," which are disposed on opposed sides of the tissue defect "D," at a plurality of fixation points (e.g., "P1-P10") via fasteners 130. FIG. 10C illustrates an implant 200''' fastened to the first and second tissues "T1" and "T2" at a plurality of separate and discrete spaced apart segments 200a-200h, for example, that each separately extend across a tissue defect "D" between two fixation points via fasteners 130. FIG. 10D illustrates an implant 200'''' secured to the first and second tissues "T1" and "T2" on opposed sides of a tissue defect "D" at a plurality of fixation points via fasteners on each side of the tissue prior to bridging the tissue defect "D." For example, the implant 200'''' is secured to the first tissue "T1" at two first fixation points "P1" and "P2," where fixation point "P1" is further from the tissue defect "D" than fixation point "P2." The implant 200'''' is then anchored to the second tissue "T2" at three second fixation points "P3-P5," where fixation point "P3" is closer to the tissue defect "D" than fixation point "P4," the implant 200'''' is folded back upon itself at fixation point "P4," and secured at fixation point "P5" which is closer to the tissue defect "D" than fixation point "P4" and in spaced relation relative to fixation point "P3." This pattern may then be repeated until the tissue defect "D" is closed.

The implants of the tissue defect closure system may be provided in a kit including a plurality of implants, for example, in tissue defect closure methods utilizing an interrupted stitching pattern (e.g., FIG. 10C).

Figure 11:
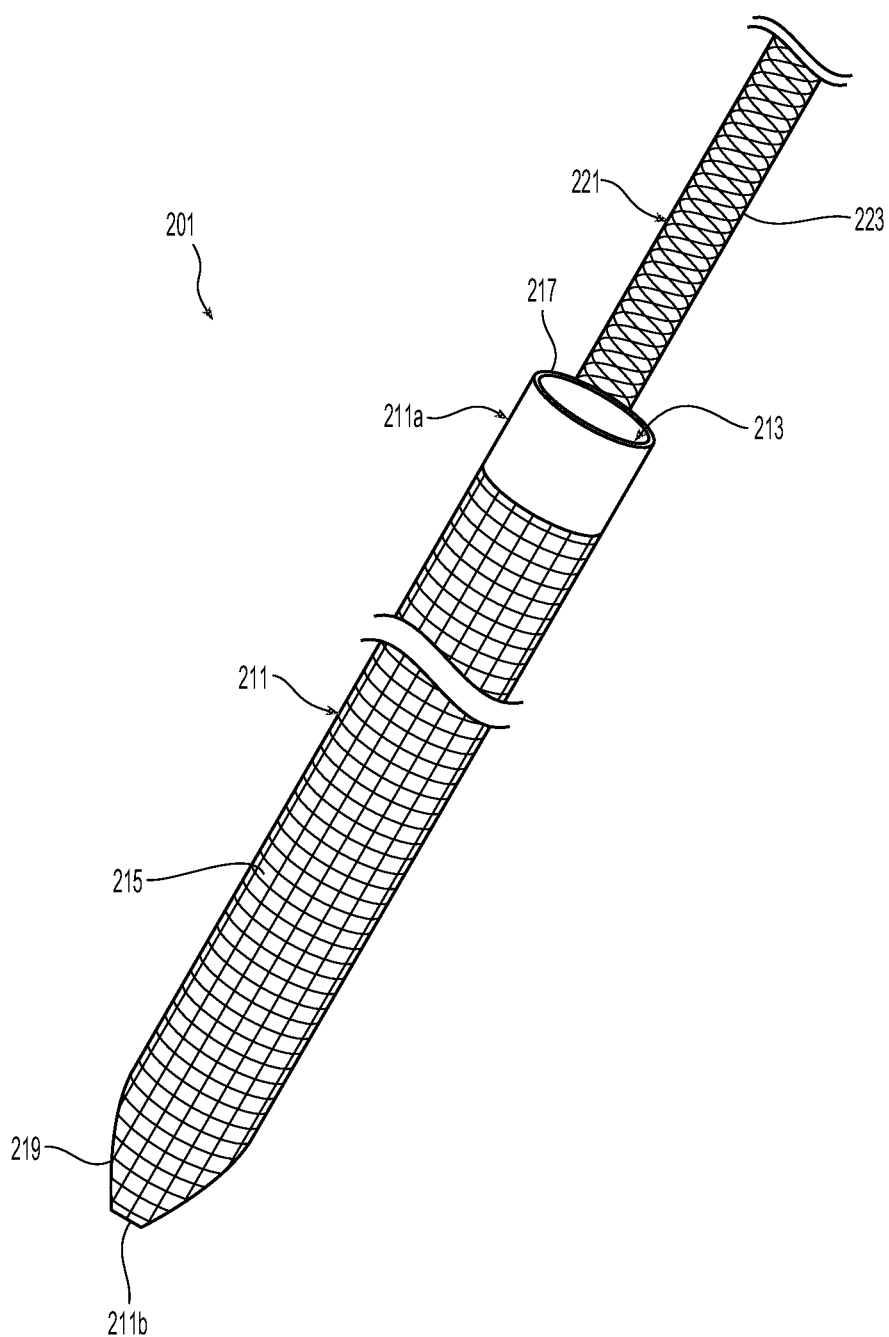
FIG. 11 is a top view of an implant in accordance with the present disclosure.

As another example, with reference now to FIG. 11, an implant 201 is accordance with the present disclosure is shown. The implant 201 is substantially similar to the implant 200 and therefore described with respect to differences therebetween. Implant 201 includes an elongated hollow body 211 having a porous structure, such as the collapsible mesh fabric, and defines an elongated pocket 213 therein. The elongated hollow body 211 includes a coating 215 disposed thereon to reduce friction between the elongated hollow body 211 during insertion into tissue and/or through a surgical instrument, such as a trocar, cannula, or access port. In embodiments, the coating 215 aids in minimizing the escape of gases in surgical procedures in which the surgical region is insufflated, for example, by helping maintain a pneumoperitoneum by minimizing pneumo leakage around a trocar seal. The coating 215 may be a lubricious coating including, for example, hydrophilic polymers, urethanes, siloxanes, and/or parylenes, among other coating materials within the purview of those skilled in the art.

The elongated hollow body 211 has an open proximal end 211a including a collar 217 and a closed distal end 211b including a tapered tip 219. The collar 217 is disposed entirely around the open proximal end 211a of the elongated hollow body 211, and is formed from a non-porous, solid material that can, for example, conform to the shape of a trocar seal to minimize the escape of gases therefrom. The collar 213 may be a biocompatible non-woven, non-braided, plastic, polymeric, and/or thermoformed material, such as, for example, polypropylene, polyethylene, polyvinylchloride, and/or ethyl vinyl acetate. A leash 221 is affixed to, and extends from, a portion of the proximal end 211a and/or collar 217 of the elongated hollow body 211 and includes an elongated body 223, such as, for example, a multifilament suture. The tapered tip 219 is defined within the distal end 211b of the elongated hollow body 211 to aid in the insertion of the elongated hollow 211 through tissue and/or a surgical instrument. The tapered tip 219 can have a continuous distally tapering profile or can include two or more distally tapered segments each having a different taper angle.

As yet another example, while the tissue defect closure system have been described for the closure of ventral hernias, other applications of such systems are additionally or alternatively possible. For example, it should be appreciated that tissue defect closure systems of the present disclosure can be used in a range of tissue repair applications including, for example, wound closure.

A number of embodiments have been described. Nevertheless, it will be understood that various modifications may be made without departing from the spirit and scope of the disclosure. Accordingly, other embodiments are within the scope of the following claims.

What is claimed is:

1. A tissue defect closure system comprising:
    an endoscopic surgical fixation device including a handle assembly and an elongated outer tube having a distal end and including a plurality of fasteners disposed therein; and
    an implant including:
        an elongated hollow body having an open proximal end and a closed distal end, and defining an elongated pocket therein, the elongated pocket dimensioned to engage the elongated outer tube of the endoscopic surgical fixation device; and
        a leash extending from the open proximal end of the elongated hollow body, the leash dimensioned to extend proximally beyond a proximal end of the elongated outer tube of the endoscopic surgical fixation device when the elongated pocket is engaged with the elongated outer tube, the leash including a proximal end terminating in a loop forming an opening therethrough, the opening being open on opposed sides of the leash.

2. The tissue defect closure system according to claim 1, wherein the elongated pocket of the implant includes an inner dimension that is complementary in size and shape with an outer surface of the elongated outer tube of the endoscopic surgical fixation device such that the implant is maintained in slidable contact with the elongated outer tube.

3. The tissue defect closure system according to claim 1, wherein the elongated pocket of the implant includes an inner dimension that is adjustable to conform to an outer dimension of the elongated outer tube of the endoscopic surgical fixation device.

4. The tissue defect closure system according to claim 1, wherein the implant is formed from a collapsible mesh fabric.

5. The tissue defect closure system according to claim 4, wherein the collapsible mesh fabric is a knitted, braided, woven, or non-woven fibrous structure.

6. The tissue defect closure system according to claim 4, wherein the collapsible mesh fabric is a biaxial or triaxial braided structure.

7. The tissue defect closure system according to claim 1, wherein the leash includes an elongated flat body.

8. The tissue defect closure system according to claim 1, wherein the leash includes an elongated rounded body.

9. The tissue defect closure system according to claim 1, wherein the plurality of fasteners are selected from the group consisting of clips, tacks, coils, anchors, and staples.

10. The tissue defect closure system according to claim 1, wherein the elongated hollow body of the implant has a coating disposed thereon.

11. The tissue defect closure system according to claim 1, wherein, when the elongated outer tube of the endoscopic surgical fixation device is positioned within the elongated pocket of the implant, the elongated hollow body extends a portion of a length of the elongated outer tube.

12. The tissue defect closure system according to claim 1, wherein the implant further includes a collar disposed around the proximal end of the elongated hollow body.

13. The tissue defect closure system according to claim 12, wherein the elongated hollow body is formed from a porous material and the collar is formed from a non-porous material.

14. The tissue defect closure system according to claim 12, wherein the collar extends to a proximal-most end of the elongated hollow body.

15. The tissue defect closure system according to claim 12, wherein the elongated outer tube of the endoscopic surgical fixation device is positioned with the elongated pocket of the implant and maintains slidable contact with the elongated outer tube.

16. An implant comprising:
    an elongated hollow body adapted to close a tissue defect, the elongated hollow body having an open proximal end and a closed distal end, and defining an elongated pocket configured to engage an elongated outer tube of an endoscopic surgical fixation device; and
    a leash extending from the open proximal end of the elongated hollow body, the leash dimensioned to extend proximally beyond a proximal end of the elongated outer tube of the endoscopic surgical fixation device when the elongated pocket is engaged with the elongated outer tube, the leash including a proximal end terminating in a loop forming an opening therethrough, the opening being open on opposed sides of the leash.

17. The implant according to claim 16, wherein the elongated hollow body has a coating disposed thereon.

18. The implant according to claim 16, further including a collar disposed around the proximal end of the elongated hollow body, the collar is formed from a non-porous material.

19. The implant according to claim 16, wherein the elongated pocket of the elongated hollow body has an adjustable inner dimension.

20. The implant according to claim 16, wherein the leash and the elongated hollow body are formed from a mesh fabric having openings defined therein, and the opening in the loop of the leash is larger than the openings defined in the mesh fabric.

* * * * *